US006492141B1

(12) United States Patent
Hunik

(10) Patent No.: US 6,492,141 B1
(45) Date of Patent: Dec. 10, 2002

(54) PROCESS FOR THE PRODUCTION OF VITAMIN B12

(75) Inventor: Jan Hendik Hunik, Rodenrijs (NL)

(73) Assignee: DSM N.V., Te Heerlen (NL)

( * ) Notice: Subject to any disclaimer, the term of this patent is extended or adjusted under 35 U.S.C. 154(b) by 0 days.

(21) Appl. No.: 09/868,607

(22) PCT Filed: Dec. 20, 1999

(86) PCT No.: PCT/EP99/10290

§ 371 (c)(1),
(2), (4) Date: Sep. 28, 2001

(87) PCT Pub. No.: WO00/37669

PCT Pub. Date: Jun. 29, 2000

(30) Foreign Application Priority Data

Dec. 18, 1998 (EP) .............................. 98204325

(51) Int. Cl.⁷ ................................ C12P 19/42
(52) U.S. Cl. .......................... 435/86; 435/170; 435/822
(58) Field of Search .......................... 435/86

(56) References Cited

U.S. PATENT DOCUMENTS 5,955,321 A * 9/1999 Bijl .............................. 435/86
6,187,761 B1 * 2/2001 Bijl .............................. 435/86

FOREIGN PATENT DOCUMENTS

| EP | 0 087 920 | | 9/1983 |
| EP | 0 668 359 | * | 8/1995 |
| EP | 0 824 152 | | 2/1998 |
| GB | 846 149 | | 8/1960 |

OTHER PUBLICATIONS

Computer Derwent Abstract 1995–370467 JP07250675 "Culture of Propionibacterium Sp. Microorganisms for Vitamin B12 Prodn by partially removing propionic acid from culture medium" Oct. 1995.*
Quesada–Chanto et al., Applied Microbiological Biotechnology (1998) 49:732–736.
Quesada–Chanto et al., World Journal of Microbiology and Biotechnology (1998) 14(6):843–846.
Ye et al., Journal of Fermentation and Bioengineering (1996) 82(5):484–491.

* cited by examiner

Primary Examiner—Herbert J. Lilling
(74) Attorney, Agent, or Firm—Morrison & Foerster LLP

(57) ABSTRACT

The present invention relates to a process for producing vitamin B12, wherein said process comprises the steps of (a) culturing a strain of the genus Propionibacterium in a first fermenter under anaerobic conditions to obtain a culture of Propionibacterium, (b) transferring at least part of the culture obtained in (a) to a second fermenter and subjecting this culture to oxygen, (c) replacing in the first fermenter part of the volume transferred in (b) with fresh culture medium and (d) repeating steps (a), (b) and (c) at least once.

16 Claims, No Drawings

PROCESS FOR THE PRODUCTION OF VITAMIN B12

FIELD OF THE INVENTION

The present invention relates to a fermentation process for the production of vitamin B12.

BACKGROUND OF THE INVENTION

Vitamin B12 is an important vitamin for humans and animals. It is used to treat pernicious anaemia and peripheral neuritis, and is used as a dietary supplement. Vitamin B12 is also an important animal feed supplement as growth enhancer.

The term vitamin B12 is used to describe compounds of the cobalt corrinoid family, in particular those of the cobalamin group. The most used compound of this group is cyanocobalamin and as such the term vitamin B12 is sometimes used to refer to cyanocobalamin. In this specification the term vitamin B12 should be attributed its broad meaning so as to include all the cobalt corrinoids of the cobalamin group, which include in particular cyanocobalamin, hydroxocobalamin, methylcobalamin and 5'desoxyadenosylcobalamin, characterised by a cyano, hydroxyl, methyl or 5'-desoxyadenosyl radical respectively. The methylcobalamin and 5'desoxyadenosylcobalamin compounds are known to be unstable to light in isolated form and are easily transformed to hydroxocobalamin in aqueous solution.

For this reason, almost all commercial vitamin B12 preparations consist of the stable cyanocobalamin, which as such is not the chemical form in which vitamin B12 can be found in nature. In this specification the term natural vitamin B12 is defined so as to comprise all chemical forms of vitamin B12 naturally occurring in nature, cyanocobalamin thus being excluded.

Vitamin B12 is produced industrially by microbial fermentation, using almost exclusively Pseudomonas denitrificans and Propionibacterium species (as reviewed by Spalla et al, 1989 "Microbial production of vitamin B12", In: Biotechnology of vitamins, pigments and growth factors, E. J. Vandamme ed., Elsevier, London, N.Y., pp. 257–284). Contrary to Pseudomonas, Propionibacteria are food-grade. Processes using Propionibacterium species thus have the advantage that they allow to formulate natural vitamin B12 together with the biomass in which it is produced, as recently described in EP-A-0 824 152. Such processes avoid the conversion of natural vitamin B12 into the cyanocobalamin form by chemical processes including cyanidisation followed by extraction and purification steps using organic solvents. The chemical conversion step and any subsequent purification steps cause this production process to be expensive, unsafe to the operators and environmentally unfriendly.

Propionibacteria are Gram-positive bacteria capable of producing valuable compounds in a variety of industrial processes. Propionibacteria are, for instance, important in the production of cheese, propionic acid, flavours and vitamin B12.

Propionibacteria are, as the name suggested, characteristic in the production of propionic acid. Glucose is commonly used as carbon source, but other substrates, i.e. fructose, mannose, galactose, glycerol and milk, can be used for growth. Besides propionic acid, acetic acid is produced under anaerobic conditions, with a ratio of 2:1 for propionic acid : acetic acid. The production of propionic acid is a clear advantage over other species as this compound is toxic in low levels for many other organisms, like lactic acid bacteria, acetic acid bacteria and yeasts. As a result there is little chance of contamination with other microorganisms during fermentation. The upper tolerance level for propionic acid for Propionibacterium is approximately 20–40 g/l (with a fermentation around pH 7): this is the level where the propionic acid starts to inhibit growth. The undissociated propionic acid is the actual toxic component for Propionibacteria, as is shown by Nanba et al. (1983, J. Ferment. Technol., 61: 551–556) for *Propionibacterium shermanii*. The specific growth rate decreases rapidly for undissociated propionic acid concentrations above 5 mM. This effect is also demonstrated by Blanc et al. (1987, Bioproc. Eng., 2: 175–179) for *P. acidi-propionici*, where the growth rate is drastically reduced above a pseudo critical value of 4 mM propionic acid. This implies that in fermentations with a pH around 7.0 propionic acid concentrations above 40 g/l are only reached with very low growth rates. This maximum amount of propionic acid produced in such fermentations results in a maximum of 25–35 g/l biomass that can be reached. Propionic acid concentration is thus one limiting factor for biomass growth and thereby for high vitamin B12 yield.

Several Propionibacterium species are capable to produce vitamin B12 in large scale fermentation processes. The process is described as a two-stage fermentation with a 72–88 hours anaerobic fermentation followed by a 72–88 hours aerobic phase. The vitamin B12 concentration in the cells rapidly increases in the aerobic phase, with typical values of 25–40 mg vitamin B12/l (see e.g. DE 1 239 694, U.S. Pat. No. 3,411,991, or in: Biochemical engineering and biotechnology handbook, 1991, B. Atkinson ed., Macmillan Publishers Ltd, pp: 1213–1220). Anaerobic growth followed by an aerobic phase with limited growth is important for economic production of vitamin B12 using Propionibacterium species. This requirement, however, limits the amount of biomass to 25–35 g/l as described above. Several attempts have been made to overcome the barrier of propionic acid toxicity in order to increase biomass and thereby the yield of vitamin B12.

Alternated anaerobic-aerobic phases are e.g. suggested to reduce the amount of acids (Ye et al., 1996, J. Ferment. Bioeng. 85: 484–491). In the aerobic phase the propionic acid is converted to less toxic acetic acid, with simultaneous formation of vitamin B12. The relative yield of vitamin B12 has been increased, but the final titre is rather low. This is probably due to inhibition early in the synthesis of vitamin B12 and/or other oxygen related products limiting the synthesis of vitamin B12. The final vitamin B12 produced with this method is 9 mg/l compared to 4.5 mg/l with the fully separated anaerobic and aerobic phases. Both values are rather low for vitamin B12 production with Propionibacteria.

The suggestion to use immobilized cells is mainly focused on the production of propionic acid (Rickert et al., 1998, Enzyme Microb. Technol. 22: 409–414). The propionic acid production is greatly enhanced. Use of this option for vitamin B12 production (which is not mentioned by Rickert et al.) will imply harvesting of the vitamin B12-containing cells with the immobilization material. This is only feasible when the additional cost for the immobilization equipment as well as the immobilization material itself are competitive with the current technology. Yongsmith et al. presented the production of vitamin B12 with immobilised cells of Propionibacterium sp. strain arl AKU1251. The maximum vitamin B12 concentrations is in the range of 14–16 mg/kg, which is no improvement of the production with freely suspended cells, as described before (Yongsmith et al. 1983, J. Ferment. Technol. 61: 593–598).

Although Propionibacteria can grow under aerobic conditions, the production of corrinoids (i.e. the general name for vitamin B12 and its precursors) is absent above a dissolved oxygen concentration of 0.19 mM=6 mg $O_2$/L. The lower the oxygen concentration the higher the corrinoid production is with a maximum corrinoid production under non-aerated conditions (Quesada-Chanto et al., 1998, Appl. Microbiol. Biotechnol. 49: 732–736). Oxygen concentration is a limiting factor for vitamin B12 synthesis.

A repeated fed-batch fermentation with an anaerobic phase followed by an aerobic phase and withdrawal of broth at the end of the aerobic phase is not possible. According to Quesada-Chanto et al. (1998), production of the corrinoids is optimal under anaerobic conditions, whereas small amounts of oxygen reduce the production of corrinoids. These findings are supported by the results obtained in example 1. A repeated fed-batch process with an aerobic and anaerobic phase in one fermenter therefore is, not economically feasible.

GB patent 846,149 describes a continuous process for the synthesis of vitamin B12. This process comprises fermenting Propionibacterium in a nutrient medium under anaerobic conditions in a first zone while adding nutrients to this zone, passing cell-containing medium from the first zone into a second zone which is under microaerobic conditions and withdrawing cell-containing medium containing vitamin B12 from this second zone. The concentration of cells and the volume of medium in both zones is maintained substantially constant by continuous fill and draw operations. This process leads to the synthesis of up to 12 mg/l of vitamin B12, which is no improvement compared with a more classical method of production.

There is thus still a need for Propionibacterium-based fermentation processes for the production of vitamin B12 with further improvements in efficiency and/or vitamin B12 yield.

DESCRIPTION OF THE INVENTION

The present invention provides a process for producing vitamin B12 (and precursors thereof having detectable vitamin B12 activity) which is not a continuous process and which comprises the steps of:

(a) culturing a strain of the genus Propionibacterium in a first fermenter under anaerobic conditions to obtain a culture of Propionibacterium, (b) transferring at least part of the culture obtained in (a) to a second fermenter and subjecting this culture to oxygen, (c) replacing in the first fermenter part of the volume transferred in (b) with fresh culture medium, and (d) repeating steps (a), (b), and (c) at least once.

In this specification the term vitamin B12 should be attributed its broad meaning so as to include all the cobalt corrinoids of the cobalamin group, which include in particular cyanocobalamin, hydroxocobalamin, methylcobalamin and 5'desoxyadenosylcobalamin, characterised by a cyano, hydroxyl, methyl or 5'-desoxyadenosyl radical respectively. The term vitamin B12 further comprises any vitamin B12 precursor having vitamin B12 activity as detectable in the turbidimetric bioassay based on the growth response of *Lactobacillus leichmanii* ATCC 7830 as described in detail in: the United States Pharmacopoeia, The National Formulary, 1995, pp. 1719–1721, United States Pharmacopoeial Convention, Inc., Rockville, Md.

One aspect of the process of the invention concerns the relation between the fraction of the anaerobic culture which is transferred in (b) and replenished with fresh medium in (c) and, on the one hand, the growth rate of the anaerobic culture (in (a)) and, on the other hand, the time interval between the subsequent withdrawals. Preferably, the withdrawal volume (which is transferred in (b) and replaced in (c)) relates to the total working volume of the first fermenter as a function of growth rate of the culture in the first fermenter and time interval between each draw according to the equation:

$$\ln\left(\frac{\text{working volume}}{\text{working volume} - \text{withdrawal volume}}\right) = growthrate * (\text{time interval between each draw})$$

In this equation the growth rate is expressed in $h^{-1}$. Typically, the growth rate may vary over the applied time interval and an average value may be applied in the formula. The time interval between each draw is expressed in hours. Preferably, the growth rate during the anaerobic phase is maintained in the range between 0.03 and 1 $h^{-1}$. The skilled person will appreciate that at constant growth rate, decreasing both the time interval and the withdrawal volume will approach a continuous process, which is not a preferred embodiment of the present invention.

One embodiment of the process of the present invention comprises the steps of:

(a) culturing a strain of the genus Propionibacterium in a first fermenter under anaerobic conditions, (b) transferring at least 30 to 90%, preferably at least 40 to 90%, more preferably at least 50 to 90%, more preferably at least 60 to 90% and most preferably at least 70 to 90% of the culture volume obtained in (a) to a second fermenter and subjecting this culture to oxygen, (c) replacing in the first fermenter the same volume as the one withdrawn in step (b) with fresh culture medium; and (d) repeating steps (a), (b), and (c) at least once.

In another preferred embodiment of the process of the invention, the culture of a strain of the genus Propionibacterium under anaerobic conditions (step (a)) leads to at least 20 g/l dry biomass, preferably at least 30 g/l, preferably at least 40 g/l, preferably at least 50 g/l, preferably at least 60 g/l, preferably at least 70 g/l, preferably at least 80 g/l, more preferably at least 90 g/l and most preferably at least 100 g/l.

Knowing the withdrawal volume and the growth rate of the microorganism used, the skilled person can easily deduce from the formula the time interval between each draw and thus the duration of the whole process.

In another preferred embodiment of the process of the invention, the dissolved Oxygen concentration at inoculation of the anaerobic phase is less than 5% of air saturation, preferably less than 2.5%, and more preferably less than 1% of air saturation.

Preferably, the anaerobic conditions of the process of the invention are such that the oxygen uptake rate during the anaerobic phase (a) is no more than 2 mmol $O_2$ $l^{-1}h^{-1}$, preferably no more than 1 mmol $O_2$ $l^{-1}h^{-1}$, and most preferably approaches zero mmol $O_2$ $l^{-1}h^{-1}$, as measured by mass-spectometry and gas flow analysis (see e.g. in: Basic Bioreactor Design, 1991, K. van't Riet & J. Tramper, eds., Marcel Dekker Inc.).

In step (b) of the process of the invention, the culture is subjected to oxygen. Preferably, the oxygen uptake rate (OUR) during this aerobic phase of the process is at least 5 mmol $O_2$ $l^{-1}h^{-1}$, more preferably at least 20 mmol $O_2$ $l^{-1}h^{-1}$, still more preferably at least 40 mmol $O_2$ $l^{-1}h^{-1}$, and most preferably at least 80 mmol $O_2$ $l^{-1}h^{-1}$.

According to one embodiment of the invention there is provided a process wherein the aerobic second phase in (b) is performed in at least two serially connected aerobic fermenters. Most preferably the aerobic second phase in (b) is performed in plug flow mode, wherein e.g. the "second" aerobic fermenter comprises a series of aerobic fermenters.

Suitable culture media for the production of vitamin B12 with Propionibacteria are well-known in the art (cf. Biochemical engineering and biotechnology handbook, 1991, B. Atkinson ed., Macmillan Publishers Ltd, pp: 1213–1220). In a preferred embodiment of the invention the culture medium is supplemented with 1–50 mM of one or more compounds selected from the group consisting of betaine, methionine and glutamine. Another preferred supplement for the culture medium is 5,6-dimethylbenzimidazole (DBI). DBI is preferably supplemented at 1–40 mg DBI per litre. Preferably, DBI is added to the culture medium at the start of the aerobic phase or during that phase.

In a preferred embodiment of the process of the invention the concentration of undissociated propionic acid is controlled such that it does not exceed 5 mM. This conveniently may be done by increasing the pH of the culture medium according to methods well known to the skilled person.

According to another embodiment of the invention, the temperature under anaerobic conditions is different from the temperature under aerobic conditions. Preferably, the temperature under anaerobic condition is higher than the temperature under aerobic conditions. More preferably, the temperature under anaerobic conditions is at least 2 degrees higher than the temperature under aerobic conditions, more preferably at least 4 degrees higher, more preferably at least 6 degrees higher, more preferably at least 8 degrees higher, more preferably at least 10 degrees higher and most preferably at least 12 degrees higher. For instance, the temperature under anaerobic conditions may be 36° C. and under aerobic conditions 24° C., or these temperatures may be 36° C. and 30° C., respectively.

In the process of the invention, preferably a strain of a Propionibacterium species is used which is selected from the group consisting of the classical or Dairy Propionibacteria as described in Bergey's manual of systematic bacteriology, 1986, J. B. Butler, Williams & Wilkins, p 1346–1353. This group comprises inter alia the species *P. freundenreichii* with subspecies freundenreichii and shermanii, *P. thoenii*, *P. jensenii* and *P. acidipropionici*. More preferably the strain *P. freundenreichii* CBS 929.97 is used. *P. freundenreichii* CBS 929.97 was deposited Jul. 10, 1997 at the Centraal Bureau voor Schimmelcultures, Baarn, The Netherlands.

In one embodiment of the invention, the process of the invention is performed using Propionibacteria strains that are genetically modified by means of classical mutagenesis and/or recombinant DNA technology. Classically mutagenised strains can be propionic acid-resistant strains of the genus Propionibacterium, such as P. shermanii NOC 11012 and *P. freudenreichii* NOC 11013, as disclosed in U.S. Pat. No. 4,544,633. A propionic acid-resistant strain of Propionibacterium is herein defined as a strain which shows approximately equal (i.e. less than 10% difference) growth rates when compared in identical media with and without 20 g propionic acid/l.

Transformed Propionibacteria strains that have been genetically modified by recombinant DNA technology are exemplified in J 08-056673.

One of the advantages of the process of the invention is the throughput increase of the fermentation. The anaerobic phase is considerably reduced. For a growth rate of 0.06 $h^{-1}$ the output of the anaerobic phase is three fermenter volumes in 72 hours, compared to one fermenter volume for the classical process. In addition, the invention reduces the turnaround time of the fermentation, with ten consecutive fills and draws, to 20% of the classical process.

Another advantage of the process of the invention is that the size of the fill and draw volumes may be relatively large. Consequently, the growth inhibiton caused by high concentration of propionic acid under anaerobic conditions does not occur, leading to an increase in the biomass and thereby an increase in vitamin B12 yield. The amount of vitamin B12 formed using the process of the invention may be 20 to as high as 200 mg/kg mesh.

EXAMPLES

Example 1

In a series of experiments on small scale we observed that small amounts of oxygen in the anaerobic phase lead to the formation of vitamin B12. The presence of vitamin B12 in the anaerobic phase and/or the presence of small amounts of oxygen in the "anaerobic phase" significantly reduced the total amount of vitamin B12 produced.

Two laboratory scale stirred tank fermenters of 10 l with a working volume of 6 l were used. Both fermentations were inoculated with 600 ml mesh from one second stage inoculum containing exponentially growing cells of *Propionibacterium freudenreichii* CBS 929.97.

The 6 l medium of the fermentation contained the following components: 120 g Difco Yeast extract, 0.6 g myo-inositol, 264 g glucose, 30 mg $CoCl_2$, 012 g Ca-Pantothenate, 12 ml Soybean oil. A glucose feed of 5 g glucose/h was started 48 hours after inoculation.

The "reference fermentation" or "ref. ferm." was performed under completely anaerobic conditions, whereas in the second fermentation a small amount of air was allowed in the "anaerobic phase".

The results are shown in Table 1.

TABLE 1

Influence of vitamin B12 and/or oxygen in the anaerobic phase on vitamin B 12 production

| Time after inoculation [h] | Gas composition (ref. ferm.) | Vitamin B12 [mg/l] (reference fermentation) | Gas composition (plus air) | Vitamin B12 [mg/l] (plus air) |
|---|---|---|---|---|
| 49 | Head space 450 ml N2/min | 1 | Head space 450 ml N2/min + sparger 100 ml air/min | 2 |
| 54 | Head space 450 ml N2/min | 1 | Head space 450 ml N2/min + sparger 100 ml air/min | 3 |
| 72 | Sparger 800 ml air/min | 1 | Sparger 800 ml air/min | 8 |
| 96 | Sparger 800 ml air/min | 13 | Sparger 800 ml air/min | 10 |
| 120 | Sparger 800 ml air/min | 15 | Sparger 800 ml air/min | 10 |
| 144 | Sparger 800 ml air/min | 15 | Sparger 800 ml air/min | 10 |

This experiment confirms that the production of vitamin B12 in Propionibacterium cells previously grown under conditions where oxygen is present in low amounts is significantly reduced. Therefore a repeated fed-batch with alternating anaerobic and aerobic phases, does not seem useful (see Ye et al. 1996).

Example 2

A 75 l Chemap fermenter was used. The fermentation was inoculated with 5 l from a second stage inoculum containing exponentially growing cells of *Propionibacterium freudenreichii* CBS 929.97.

The medium of the fermentation contained the following components: 15 g/l Expresa Yeast extract, 50 g/l glucose, 5 mg/l $CoCl_2$. After 72 hours of anaerobic growth 50% of the fermenter content was removed and replenished with 50% fresh medium. This procedure was repeated at 96 h, 120 h and 144 h. The withdrawals are numbered as 1,2,3 and 4. This anaerobic material, with the addition of 25 mg/kg 5,6 dimethylbenzimidazole, was aerated for 72 h in a separate fermenter. The results are shown in Table 2.

TABLE 2

Development of vitamin B12 concentrations in each aerated draw.

|  | Draw 1 Vitamin B12 mg/l | Draw 2 Vitamin B12 Mg/l | Draw 3 Vitamin B12 mg/l | Draw 4 Vitamin B12 mg/l |
|---|---|---|---|---|
| Immediately after the draw | 0.5 | 0.8 | 1 | 2.5 |
| 24 h aeration | 14 | 13 | 10.7 | 7.5 |
| 48 h aeration | 14.2 | 14.2 | 10.7 | 7.5 |
| 72 h aeration | 15 | 13.4 | 10.8 | 7.5 |

Table 2 shows that the "Fill and Draw" principle is functional. However, the vitamin B12 concentration at the end of the anaerobic phase should preferably be below 1 mg vitamin B12/l for an optimal result. Vitamin B12 already formed in the anaerobic phase is indicative of a reduced vitamin B12 production in the subsequent aerobic phase and results in a reduced overall-yield of vitamin B12.

Example 3

A similar set up was used as in Example 2. After 72 hours of anaerobic growth 50% of the fermenter content was removed and replenished with 50 % fresh medium. This procedure was repeated with various interval times and withdrawal volumes for 9 times. The withdrawals are numbered as 1 to 9. This anaerobic material, with the addition of 25 mg/kg 5,6 dimethylbenzimidazole, was aerated for 72 h in a separate fermenter. The results are shown in Table 3.

TABLE 3

Withdrawal volume, time interval, vitamin B12 concentration before aeration and final vitamin B12 concentration.

| Draw number | time [h] since previous draw | Volume [%] of the withdrawal | Vitamin B12 before aeration [mg/l] | Vitamin B12 end of aeration [mg/l] |
|---|---|---|---|---|
| 1 | 72 | 50 | 0 | 15 |
| 2 | 24 | 50 | 1 | 17 |
| 3 | 12 | 50 | 0.6 | 16.3 |
| 4 | 16 | 50 | 2.8 | 14.4 |
| 5 | 16 | 50 | 3.3 | 12.2 |
| 6 | 24 | 75 | 0.9 | 10.3 |
| 7 | 24 | 75 | 1.1 | 10.6 |
| 8 | 24 | 75 | 0.4 | 12.8 |
| 9 | 24 | 75 | 8.5 | 10.2 |

This experiment demonstrates that a successful "Fill and Draw"-schedule with 50% volume withdrawal each 12 h is possible. The vitamin B12 production is comparable to the process described in the reference fermentation in Example I, when the Vitamin B12 concentration end of the anaerobic phase is below 1 mg Vitamin B12/l. Clearly, strictly limiting the oxygen concentration during the anaerobic phase, and thereby limiting the formation of vitamin B12 during this phase, is advantageous with respect to vitamin B12 yield in the subsequent aerobic phase.

Example 4

A 75 L Chemap fermenter was used in this experiment. The fermentation was inoculated with 5L from a second stage inoculum. Containing exponential growing cells of *Propionibacterium freudenreichii* spp. Freudenreichii CBS 929.97. The medium of the fermentation contained the following components: 15 g/L Expresa Yeast extract, 50 g/L glucose, 5 mg/L $CoCl_2$ and some trace elements. After 72 hours of anaerobic growth 40% of the fermenter content was removed and replenished with 40% fresh medium. This procedure was repeated 9 times with a 12 h interval. The withdrawals are numbered as 1 to 9. This anaerobic material, with the addition of 25 mg/kg 5,6 dimethylbenzimidazole, was aerated for 72 h in a separate fermenter. The results are shown in Table 4.

TABLE 4

Withdrawal volume every 12 hours, vitamin B12 concentrations before aeration and final vitamin B12 concentrations reached in aerated draw 1, 3, 5, 7 and 9.

| Draw number | Volume [%] of the withdrawal | Vitamin B12 Before aeration [mg/l] | Vitamin B12 end of aeration [mg/l] |
|---|---|---|---|
| 1 | 40 | 2 | 17 |
| 3 | 40 | 1 | 18 |
| 5 | 40 | 1 | 19 |
| 7 | 40 | 1 | 18.5 |
| 9 | 40 | 1 | 19 |

This experiment demonstrates that a successful "Fill and Draw"-schedule with 40% volume withdrawal each 12 h is possible. The vitamin B12 production is constant during over the whole experiment. Decreasing the withdrawal volume compared to the 50% in example 3 is advantageous with respect to the vitamin B12 concentration reached at the end of the aerobic phase.

What is claimed is:

1. A process for producing vitamin B12 and precursors thereof having detectable vitamin B12 activity, which is not a continuous process and which comprises the steps of:
    (a) culturing a strain of the genus Propionibacterium in a first fermenter under anaerobic conditions to obtain a culture of Propionibacterium,
    (b) transferring at least part of the culture obtained in (a) to a second fermenter and subjecting this culture to oxygen,
    (c) replacing in the first fermenter at least part of the volume transferred in (b) with fresh culture medium; and
    (d) repeating steps (a), (b), and (c) at least once,
    wherein the process is not a continuous process for producing vitamin B12 and the precursors thereof.

2. The process of claim 1, wherein in step (b), at least 30% of the culture volume obtained in (a) is transferred to said second fermenter.

3. The process of claim 1, wherein a growth rate is maintained during step (a) in the range between 0.03 and 1 $h^{-1}$.

4. The process of claim 1, wherein the oxygen uptake rate in (a) is no more than 2 mmol $O_2$ $l^{-1}h^{-1}$, as measured by mass-spectometry and gas flow analysis.

5. The process of claim 1, wherein the oxygen uptake rate in (b) is at least 5 mmol/l/h.

6. The process of claim 1, wherein the culture medium is supplemented with a compound selected from the group consisting of betaine, methionine and glutamine.

7. The process of claim 6, wherein said culture medium is further supplemented with 1–40 mg 5,6-dimethylbenzimidazole per litre.

8. The process of claim 1, wherein the pH of the culture medium is increased such that the concentration of undissociated propionic acid does not exceed 5 mM.

9. The process of claim 1, wherein the temperature under anaerobic conditions is higher than the temperature under aerobic conditions.

10. The process of claim 9, wherein the temperature under anaerobic conditions may be 36° C. and under aerobic conditions 24° C.

11. The process of claim 1, wherein the strain is of a Propionibacterium species selected from the group consisting of *P. freundenreichii*, with subspecies *freudenreichii* and *shermanii*, *P. theonii*, *P. jensenii*, and *P. acidipropionici*.

12. The process of claim 11, wherein the strain is *P. freundenreichii* CBS 929.97.

13. The process of claim 1, wherein the strain is a propionic acid-resistant strain of the genus Propionibacterium, *P. shermanii* NOC 11012, and/or *P. freundenreichii* NOC 11013.

14. The process of claim 13, wherein said strain is *P. shermanii* NOC 11012 and/or *P. freundenreichii* NOC 11013.

15. The process of claim 2, wherein in step (b), at least 30%–90% of the culture volume obtained in (a) is transferred to said second fermenter.

16. A process for producing vitamin B12 and precursors thereof having detectable vitamin B12 activity, which is not a continuous process and which comprises the steps of:

(a) culturing a strain of the genus Propionibacterium in a first fermenter under anaerobic conditions to obtain a culture of Propionibacterium.

(b) transferring at least part of the culture obtained in (a) to a second fermenter and subjecting this culture to oxygen.

(c) replacing in the first fermenter at least part of the volume transferred in (b) with fresh culture medium; and (d) repeating steps (a), (b), and (c) at least once,
wherein the process is not a continuous process based on variables in an equation of $$\ln\left(\frac{\text{working volume}}{\text{working volume} - \text{withdrawal volume}}\right) =$$

(growth rate) ∗ (time interval between each draw).

* * * * *